United States Patent
Moctezuma et al.

(10) Patent No.: US 10,517,680 B2
(45) Date of Patent: Dec. 31, 2019

(54) AUTOMATIC IDENTIFICATION OF INSTRUMENTS

(71) Applicant: Medtronic Navigation, Inc., Louisville, CO (US)

(72) Inventors: Joseph Moctezuma, Golden, CO (US); Craig Drager, Jacksonville, FL (US); Joseph Thomas Cilke, Broomfield, CO (US); Victor D. Snyder, Erie, CO (US); Wei-Shyang Yang, Lafayette, CO (US); Justin Kemp, Erie, CO (US); Andrew Wald, Denver, CO (US); Jerald Lamont Redmond, Germantown, TN (US); Shai Ronen, Louisville, CO (US); Nikhil Mahendra, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 15/963,407

(22) Filed: Apr. 26, 2018

(65) Prior Publication Data
US 2018/0310996 A1 Nov. 1, 2018

Related U.S. Application Data

(60) Provisional application No. 62/491,599, filed on Apr. 28, 2017.

(51) Int. Cl.
*A61B 34/20* (2016.01)
*A61B 90/98* (2016.01)
(Continued)

(52) U.S. Cl.
CPC .............. *A61B 34/20* (2016.02); *A61B 5/06* (2013.01); *A61B 34/25* (2016.02); *A61B 90/361* (2016.02); *A61B 90/37* (2016.02); *A61B 90/92* (2016.02); *A61B 90/94* (2016.02); *A61B 90/96* (2016.02); *A61B 90/98* (2016.02);
(Continued)

(58) Field of Classification Search
None
See application file for complete search history.

(56) References Cited

U.S. PATENT DOCUMENTS 6,223,137 B1 * 4/2001 McCay ................. G06Q 10/10
702/184
7,697,972 B2 4/2010 Verard et al.
(Continued)

OTHER PUBLICATIONS

Kusuda et al., Measurement of Magnetic Field from Radio-frequency Identification Antenna for Use in Operation Room, 2017, IEEE, 978-1-5090-5028-4/17/$31.00, pp. 414-415 (Year: 2017).*
(Continued)

*Primary Examiner* — Carlos Garcia
(74) *Attorney, Agent, or Firm* — Harness Dickey

(57) ABSTRACT

A system and apparatus is disclosed to automatically determine the identification and selected information relating to instruments. The identification information may be read or determined by various reader systems and then transferred for various purposes. The identification information may be stored on the instrument with a storage system or printing and/or recalled from a memory once the identification is made.

21 Claims, 3 Drawing Sheets

(51) Int. Cl.

| | |
|---|---|
| *A61B 90/96* | (2016.01) |
| *A61B 34/00* | (2016.01) |
| *A61B 5/06* | (2006.01) |
| *A61B 90/00* | (2016.01) |
| *A61B 90/92* | (2016.01) |
| *G06K 9/00* | (2006.01) |
| *G06K 9/46* | (2006.01) |
| *G06K 9/62* | (2006.01) |
| *A61B 90/94* | (2016.01) |
| *A61B 34/10* | (2016.01) |

(52) U.S. Cl.
CPC ....... *G06K 9/00624* (2013.01); *G06K 9/4628* (2013.01); *G06K 9/6271* (2013.01); *A61B 2034/107* (2016.02); *A61B 2034/2051* (2016.02); *A61B 2034/2055* (2016.02); *A61B 2034/2065* (2016.02); *A61B 2034/254* (2016.02); *A61B 2034/256* (2016.02); *A61B 2090/365* (2016.02); *A61B 2090/374* (2016.02); *A61B 2090/376* (2016.02); *A61B 2090/3762* (2016.02); *G06K 2209/057* (2013.01)

(56) References Cited

U.S. PATENT DOCUMENTS

| | | | |
|---|---|---|---|
| 8,233,963 B2 | 7/2012 | Hartmann et al. | |
| RE44,305 E | 6/2013 | Foley et al. | |
| 8,600,478 B2 | 12/2013 | Verard et al. | |
| 8,644,907 B2 | 2/2014 | Hartmann et al. | |
| 8,842,893 B2 | 9/2014 | Teichman et al. | |
| 9,226,686 B2* | 1/2016 | Blair | A61B 5/062 |
| 9,265,589 B2 | 2/2016 | Hartmann et al. | |
| 2002/0067263 A1* | 6/2002 | Tafoya | A61B 90/98 |
| | | | 340/572.1 |
| 2003/0101375 A1* | 5/2003 | Hohn | G16H 40/40 |
| | | | 714/25 |
| 2004/0199072 A1 | 10/2004 | Sprouse et al. | |
| 2008/0200926 A1 | 8/2008 | Verard et al. | |
| 2008/0200927 A1 | 8/2008 | Hartmann et al. | |
| 2013/0245389 A1* | 9/2013 | Schultz | A61B 5/0002 |
| | | | 600/301 |
| 2014/0131454 A1* | 5/2014 | Weisshaupt | A61B 90/98 |
| | | | 235/492 |
| 2014/0243623 A1* | 8/2014 | Kersting | A61F 9/007 |
| | | | 600/301 |
| 2015/0190202 A1* | 7/2015 | Weinert | G06K 7/10366 |
| | | | 340/5.8 |
| 2015/0297307 A1* | 10/2015 | Sweeney | G06Q 10/087 |
| | | | 705/2 |
| 2016/0162782 A1* | 6/2016 | Park | G06N 3/0454 |
| | | | 706/17 |
| 2017/0312035 A1* | 11/2017 | May | A61B 50/26 |
| 2019/0206576 A1* | 7/2019 | Shelton, IV | G06T 11/206 |
| 2019/0207857 A1* | 7/2019 | Shelton, IV | G16H 20/40 |

OTHER PUBLICATIONS

Hanada et al., Improving Efficiency through Analysis of Data Obtained from an RFID Tag System for Surgical Instruments, 2015, IEEE, 978-1-4799-8748-1/15/$31.00, pp. 84-87 (Year: 2015).*

Hanada et al., Introduction of an RFID Tag System to a Large Hospital and the Practical Usage of the Data Obtained, 2015, IEEE, 978-1-4799-8072-7/15/$31.00, pp. 108-111 (Year: 2015).*

Sawa et al., Shimane University Hospital implements RFID technology to manage surgical instruments, 2013, IEEE, 978-1-4673-5772-2/13/$31.00 (Year: 2013).*

Amucucchi et al., Usage of RFId in safety applications, 2017, IEEE, 978-1-5386-3917-7/17/$31.00 (Year: 2017).*

Rivera et al., ASSIST—Automated System for Surgical Instrument and Sponge Tracking, Apr. 16-17, 2008, IEEE, 978-1-4244-1712-4/08/$25.00, pp. 297-302 (Year: 2008).*

Nandita et al., Efficient Life Saving System to Track Surgical Instruments, 2012, IEEE, 978-1-4673-4634-4/12/$31.00, pp. 20-23 (Year: 2012).*

Bova, Computer Based Guidance in the Modern Operating Room: A Historical Perspective, Date of publication Oct. 25, 2010, IEEE, IEEE Reviews in Biomedical Engineering, vol. 3, pp. 209-222 (Year: 2010).*

Hazleburst et al., Getting the Right Tools for the Job: Distributed Planning in Cardiac Surgery, Nov. 6, 2004, IEEE, IEEE Transactions on Systems, Man, and Cybernetics—Part A: Systems and Humans, vol. 34, No. 6, pp. 708-717 (Year: 2004).*

Helm et al., Spinal Navigation and Imaging: History, Trends, and Future, Aug. 8, 2015, IEEE, IEEE Transactions on Medical Imaging, vol. 34, No. 8, pp. 1738-1746 (Year: 2015).*

Chung et al., A Robot-Assisted Surgery System for Spinal Fusion, 2005, IEEE, IEEE/RSJ International Conference on Intelligent Robots and Systems (Year: 2005).*

U.S. Appl. No. 15/963,426, filed Apr. 26, 2018, Moctezuma et al.

Krizhevsky, et al., ImageNet Classification with Deep Convolutional Neural Networks, Advances in Neural Information Processing Systems 25 (NIPS 2012).

International Search Report and Written Opinion dated Jul. 26, 2018 in corresponding/related International Application No. PCT/US2018/029916.

International Search Report and Written Opinion dated Jul. 26, 2018 in corresponding/related International Application No. PCT/US2018/029928.

* cited by examiner

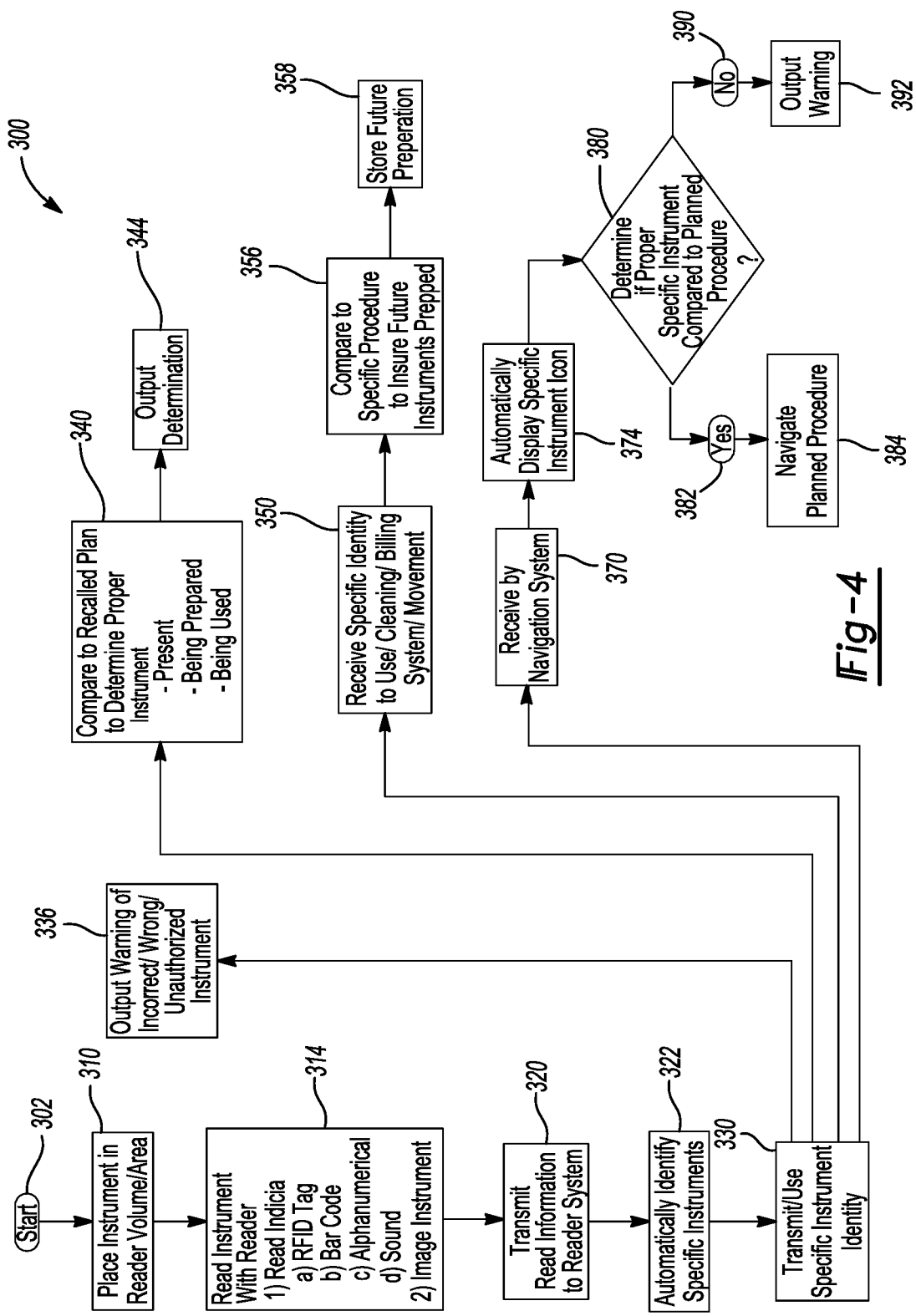

AUTOMATIC IDENTIFICATION OF INSTRUMENTS

CROSS-REFERENCE TO RELATED APPLICATIONS

This application claims the benefit of U.S. Provisional Application No. 62/491,599, filed on Apr. 28, 2017. This application includes subject matter related to U.S. patent application Ser. No. 15/963,426 and published as U.S. Pat. App. Pub. No. 2018/0311012. The entire disclosure(s) of (each of) the above application(s) is (are) incorporated herein by reference.

FIELD

A system for identification of an instrument, and particularly to a system and method for providing and/or transferring specific information regarding a particular instrument.

BACKGROUND

The statements in this section merely provide background information related to the present disclosure and may not constitute prior art.

Surgical procedures are often performed on various patients in various operating theaters at different times. Many instruments are used during a single procedure. The instruments used during a specific procedure, however, are generally specific to that procedure. Further, many instruments are reused for similar or identical procedures (e.g. spinal implant placement) on different patients at different times. It may be desirable to provide information relating to a specific instrument or attachment (e.g. tip) to an instrument among the multiple instruments brought into or provided in a single operating theater, or a single procedure, or among multiple procedures with a single instrument.

A manual system may require a user or an assistant to enter or record information about an instrument, such as a surgical instrument. The entered information relates general use and inventory tracking about a particular instrument. The information can be transferred to a computer to determine the location of a selected instrument in an inventory, a manufacturer of an instrument, or the like. The information relating to the instrument, however, is generally limited to information relating only to inventory tracking information or limited identity information.

SUMMARY

A system, including an automatic identification system, can provide information about an instrument including its specific type, size, number of uses, use during a procedure, preparation for a procedure, etc. The information may be automatically entered or sent to a surgical navigation system. The surgical navigation system may include a tracking system that tracks a location (e.g. position and orientation) in a surgical space during a specific or current procedure. The tracking information may be used in combination with the automatically provided identification information for use by the navigation system to properly and accurately track a specific location of at least a portion of the instrument.

Identification information may include calibration information, size information, configuration information, and the like that can be transferred to the navigation system from a specific instrument directly. The identification information can include information specific to a particular procedure about a particular instrument to allow for precise tracking of the instrument during the procedure. The identification system can also allow for writing, rewriting, overwriting, or deleting identification information to insure up-to-date and accurate information, particular procedure information, and the like are always provided and correct.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 4 is a flow/use chart of an automatic identification system.

Corresponding reference numerals indicate corresponding parts throughout the several views of the drawings.

DETAILED DESCRIPTION

The following description is merely exemplary in nature and is not intended to limit the present disclosure, application, or uses.

Figure 1:
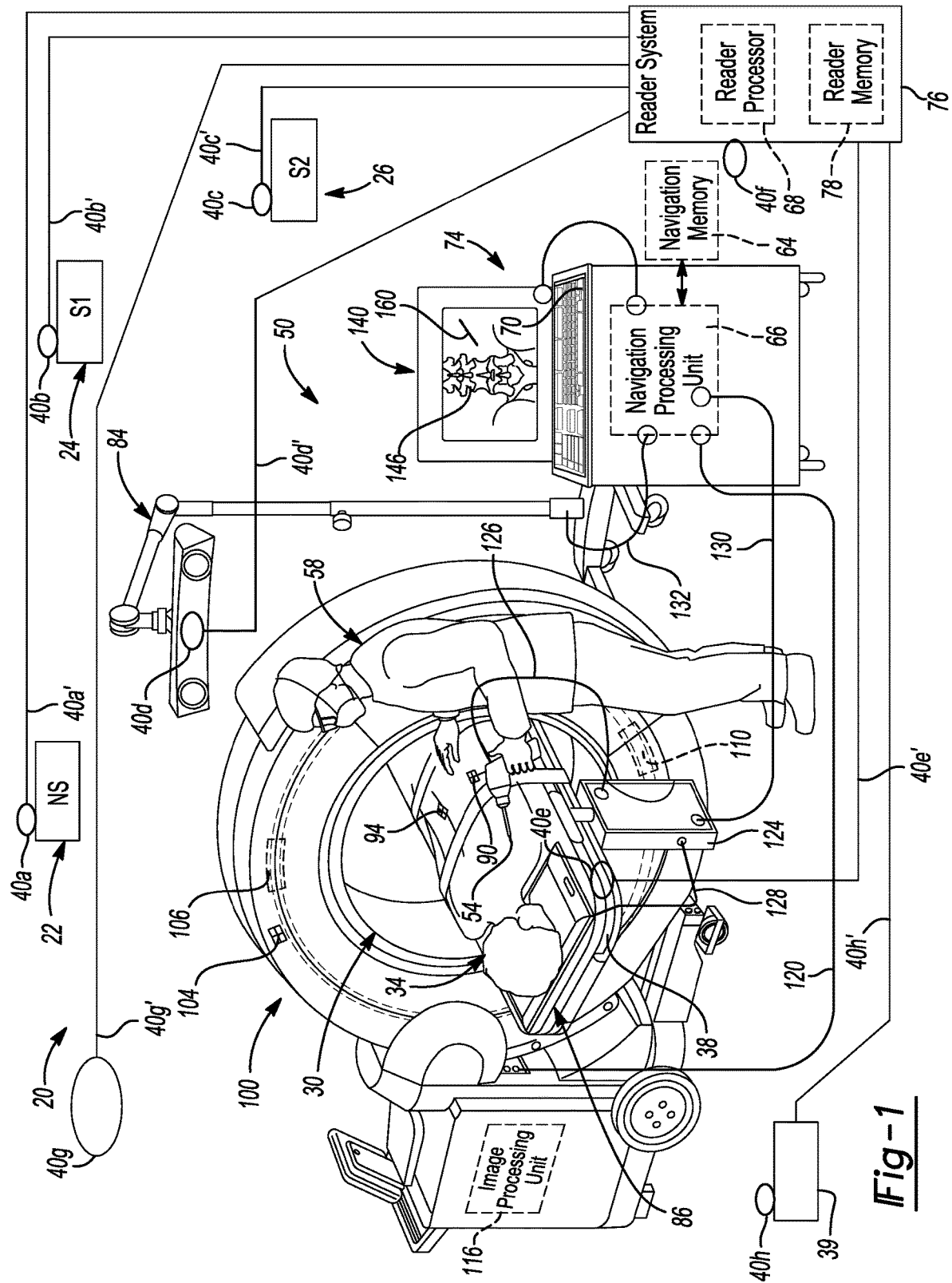
FIG. 1 is an environmental view of an operating room theater including a surgical navigation system, according to various embodiments.

With initial reference to FIG. 1 a procedure room or theater 20 as illustrated. The procedure room 20 may include a surgical operating theater as is generally understood by one skilled in the art. It is understood, however, that the area or room 20 may be any appropriate room and include any appropriate area, including those discussed herein. The surgical operating theater may include various areas or staging tables including a first table or non-sterile table or area 22. A second staging area 24 that may include a first sterile table or staging area 24 and a third table staging or area 26, which may also be a sterile area. Each of the tables or staging areas may be used for various portions or preparations for a procedure.

In various embodiments, the non-sterile table 22 may be for holding or storing sterilized and/or sterilely packaged instruments to be used during a selected procedure. The instrument may be delivered to the table 22 from a storage area that may be onsite or offsite. A user or assistant during a procedure may have access to the nonsterile table 22 to move or prepare instruments for a procedure, such as opening a package of a sterile instrument or accessing an instrument tray. The first sterile table 24 may be a staging area for placing instruments that are to be used during a selected procedure that had been opened or unwrapped in preparation for use during the procedure. Sterile area 26 may be for positioning instruments immediately prior to being used during a selected procedure and moved into a surgical volume or arena 30. In addition, a further sterile staging area may be positioned substantially adjacent to a patient or subject 34 such as on or adjacent to an operating room table or patient support 38. In addition, a used or after use table or area 39 may also be present for locating or placing instruments after use in the operating arena 30.

At each of the various locations, including the nonsterile table 22, the first sterile table 24, the second sterile table 26, and the operating arena 30, and the after use area 39 one or more reading or identification systems or readers 40 may be provided. Readers may include those disclosed in U.S. Pat. Nos. 8,233,963; 8,600,478; and/or 9,265,589, all incorporated herein by reference. In various embodiments, a first reader 40*a* may be positioned to near the nonsterile region 22. A second reader 40*b* may be positioned at or near the first sterile table 24. A third reader 44*c* may be positioned at the second sterile table 26. Further readers may include a fourth reader 40*d* positioned at or near, such as to view or read, the operating arena 30 including the subject 34. Further a reader 40*e* may be positioned on or at the operating room table 38. Other readers, as discussed herein, may also be placed at other locations. For example, a reader 40*f* may be moveable to multiple selected locations. A large area reader 40*g* may be placed to read or view a large portion and/or all of the operating theater 20. Also, a reader 40*h* may be placed at or near the used area 39.

One skilled in the art will understand that each of the readers 40*a*, 40*b*, 40*c*, 40*d*, 40*e*, 40*g*, 40*h* may be substantially identical or different, as discussed herein. Moreover, discussion of readers 40 may be refer to any or all of the readers 40*a*-40*h* unless otherwise specified. Moreover, it is not necessary that the operating theater 20 include only or all of the readers 40*a*-40*h* as discussed above. The operating theater 20 may include less readers 40 depending upon selected procedures and uses. Nevertheless, the readers 40 may be used, as discussed herein, with a navigation system 50 to assist in tracking a location of at least a portion of an instrument 54 prior to and during use of the instrument 54 on the patient 34.

In various embodiments, the instrument 54 may be transferred amongst each of the locations, such as from the nonsterile table 22, to either or both of the sterile tables 24 and 26, either in series or only to one, and to the operating region or area 30. The movement of the instrument 54 may be based upon instructions of a procedure (e.g. a preplanned and or saved plan for a procedure, such as a surgical plan) or instructions of a user, such as a surgeon 58 during a selected procedure. Each of the readers 40 and/or the large area reader 40*g* may read information regarding the instrument at any selected location and determine with a reader system 76, as discussed herein, to identify that the instrument 54 is at the location.

Movement of the instrument may be based on various purposes. For example, the surgeon 58 may instruct an assistant, such as a scrub nurse or tech, a representative, or other appropriate individual to move the instrument 54. The selected instrument 54 may be selected based upon a predetermined procedure or plan for the procedure. The procedure may be planned based upon instructions from the user 58, or in combination with other known instructions, and saved in a memory, such as a navigation memory 64. The navigation memory 64 may be accessed by a navigation processing unit 66 either alone or in combination with a reader processing unit 68. The reader processor 68 may be incorporated into a system, including either the navigation system or work station 74 or a reader system 76 which may be included internally or have a separately accessible reader memory 78.

It is understood that the processors or processing units, such as those discussed herein may include any appropriate processing unit such as an application specific processor including an application specific integrated circuit "basic" and/or general purpose processor that is configured to execute instructions that may be stored on one or more of the memories, including navigation memories 64 or the reader memories 78. Further, the memories, such as the navigation memory 64 or the reader memory 78 may be any appropriate memory such as a non-transitory computer memory including a spinning disc, solid state memory, random access memory, network or offsite accessible memory, or the like.

The operating theater 20 may include the navigation system 50 having one or more tracking systems. A first tracking system may include an optical localizer 84 that is configured to track and determine locations of optical tracking devices. Alternatively, or in addition to the optical localizer 84, an electric magnetic localizer 86 may be used to generate and/or receive electric magnetic fields to determine a location of electric magnetic tracking devices (e.g. conductive coils). A tracking device 90 may be associated with or connected to the instrument 54. The navigation system 50 may track a location (e.g. a position and orientation) of the tracking device 90. Navigation system, including tracking of tracking devices, registration of locations of patient or procedure space relative to an image space. Operation of navigation systems are generally known and disclosed in U.S. Pat. Nos. RE44,305; 7,697,972; 8,644,907; and 8,842,893; and U.S. Pat. App. Pub. Nos. 2004/0199072, all incorporated herein by reference. Navigation systems may also include the StealthStation® S7® surgical navigation system sold by Medtronic Navigation, Inc. having a place of business in Colorado, U.S.A.

A patient tracking device 94 may be connected to the patient 34 and may be referred to as a dynamic reference frame (DRF). An imaging system 100 may be used to acquire images of the subject 38, such as x-ray images. The imaging system may include the O-Arm® imaging system sold by Medtronic Navigation, Inc. having a place of business in Colorado, U.S.A. Other appropriate imaging systems may include magnetic resonance imaging (MRI) system, computed tomography (CT) imaging systems, or the like. It is understood that the imaging system 100 may not be incorporated or included in the operating theater 20, but image data may be acquired of the subject 34 before, during, or after a procedure. The image data may be used to generate one or more images, as discussed herein. An imaging tracking system 104 may also be provided to assist in registration of the images with the subject 34 in the operating space 30.

The imaging system 100 may further include a source 106, such as an x-ray source and detector 110 such as an x-ray detector. The imaging system 100 may include an imaging system processor 116 that may be used to assist in processing images. Further the images may be transmitted from the imaging system 100, such as imaging processor 116 with a transmission system 120 that may be wired or wireless and/or include a physical media transfer. The instrument, including at least the tracking device 90, may be connected to a controller 124 with a communication system 126, including a wired or wireless. Further, the EM localizer 86 may be connected to the controller 124 with a communication system 128, including a wired or wireless system. The controller 124 may also be connected to the navigation processing unit 66 with communication system 130, that may be wired or wireless. Further, the optical localizer 84 may also be in communication with a communication system 132 with the navigation processing unit 66 that may also be wired or wireless.

The navigation work station or computer system 74, which may include or be in communication with the navigation processing unit 66, may also include a display device or monitor 140. The monitor 140 may display an image 146 that is based upon or reconstructed for the image data acquired with the imaging system 100. Further, the work station system 74 may include various inputs such as a keyboard 150 or other appropriate physical (e.g. human) inputs including a mouse, foot pedal, microphone, and the like. The navigation system 50, including the work station 74, may further display an icon 160 that represents the instrument 54 based upon information from the reader 40 and the tracked location of the tracking device 90. The reader 40 may be used with the reader system 76 to provide a specific and unique identity of the instrument 54 automatically to the navigation system 50 and/or other systems, as discussed herein. The icon 160 may, therefore, be represented either as a graphical representation that looks substantially identical to instrument 54 or at least a representation of a selected location, including a tracked location of an operative portion of the instrument 54.

The various areas of the operating room theater 20, as noted above, may be monitored individually by one or more readers 40, as noted above. In various embodiments, one or a limited number of readers may read the entire operating theater 20, such as the large area reader 40g. The reader 40, according to various embodiments, therefore, may be used to monitor a single area and may have a small or tight read and/or right volume, such as a substantially equivalent to the operational area 30 and/or one of the table or staging areas 22, 24, 26. A small read/write area may be about 10 centimeters (cm) to about 35 cm from the individual reader 40. The single large area reader 40g may have a read and/or right volume that is substantially equivalent to the operating room 20, including about 3 meters (m) to about 5 m from the reader 40g. Although the single read member 40g may be provided to read or encompass a large area, it may be provided to read the volume or area in which all of the relevant action occurs, such as in the non-sterile or sterile tables 22, 24, 26 and/or the operating volume 30. The large area reader may be a reader or antenna such as an Impinj Speedway xArrar UHF RFID reader, sold by atlasRFIDstore having a place of business at Birmingham, Ala. As discussed herein, the reader 40 may be used to monitor one or both of the position and identify of instruments, including the instrument 50, within the operating theater 20 for various purposes such as determining and/or confirming a specific identity of the instrument, use of the instrument 54, movement or preparation of the instrument 54, etc. For example, in a small area reader 40, the reader system 76 may determine which reader 40 is able to read the instrument and thus a relative location of the instrument, such as at the non-sterile area 22 or at the second sterile area 26.

Further, each of the readers may include a transmission or communication systems, respectively, with the reader system 76. The communication systems may be any appropriate type of communication such as a wireless communication (e.g., Bluetooth® communication protocols and systems, wireless area network, radio frequency transmission, etc.) and/or may include wired communication systems. Regardless, each of the readers 40a-40h may include respective communication systems 40a'-40h'.

Figure 2:
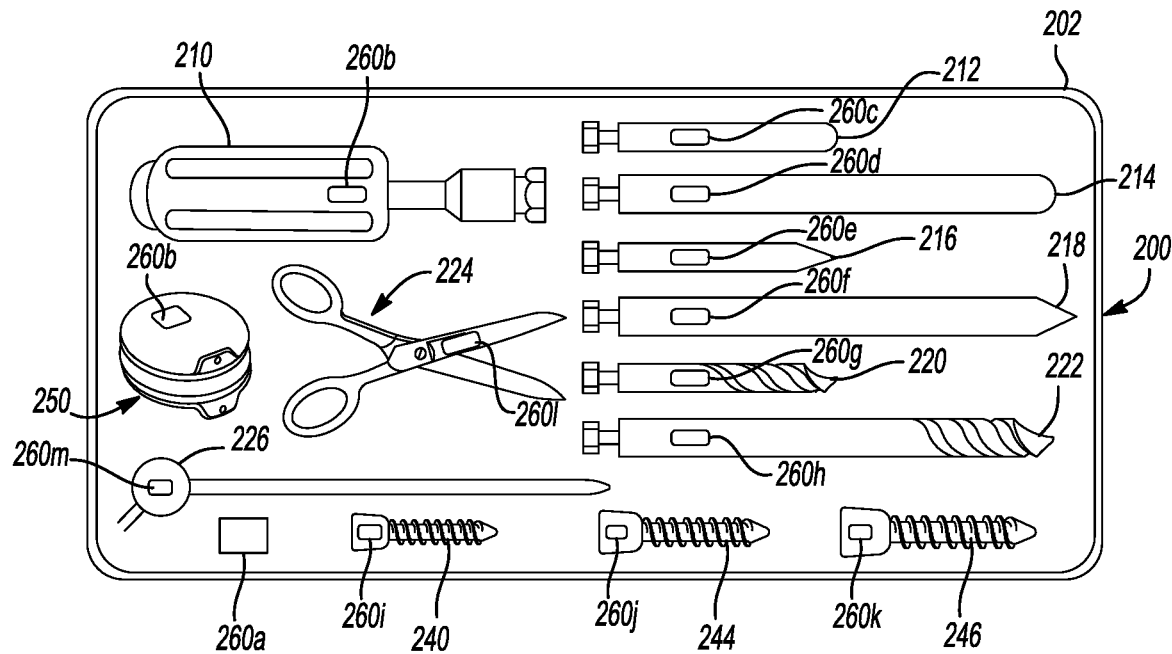
FIG. 2 is a plan view of a plurality of instruments in a it, according to various embodiments.

With continued reference to FIG. 1 and additional reference to FIG. 2, an instrument kit 200 may include one or more members that may be instrument 54. As discussed herein, each member may be a specific an unique instrument that may be identifiable with the reader system 76, according to various embodiments. Thus, discussion of the tools and/or members within the kit 200 may be generally referred to as the instrument 54 unless referring to one or more specific instruments. Further, it is understood by one skilled in the art, that instruments need not be included in a kit, a single kit, or multiple kits may be provided individually as well.

Nevertheless, the instrument kit 200 may include a tray or other container 202 that holds one or more of the instruments (generally referred to as instrument 54) that may be used during a selected procedure. The tray 202, however, is understood to be optional and need not be provided. For example, the tray 202 may include a plurality of instruments including a handle or driver 210. The instrument may include both the handle 210 and an attachment or tip, such as a first probe 212, or may include only the tip or attachment. In various embodiments, as discussed herein, the handle 210 may have the tracking device 94 attached thereto during a procedure. The tracking device 90 may include an optical tracking device, electromagnetic tracking device, or other appropriate tracking device. Nevertheless, the handle 210 may have the tracking device attached at a selected and known position so that the navigation system 50 is able to illustrate the icon 160 at an appropriate location relative to the image 146 to accurately show the tracked location of at least a tip of the instrument 212 for display on the display and for performing a procedure.

Accordingly, the first instrument 212 may include a first probe and a second instrument 214 may include a second probe. The difference between the first probe 212 and the second probe 214 may be length, diameter, or other physical characteristics. The instrument kit 200 may further include a third instrument 216 and a fourth instrument 218. The difference between the third and fourth instrument 216, 218 may also be various dimensions, such as a length, diameter, or the like. The third and fourth instruments 216, 218 may be different sized awls. The instruments may further then include taps such as a fifth instrument 220 and a sixth instrument 222. The fifth and sixth instruments 220, 222 may also differ in diameter or length. For example, the fifth instrument 220 may be a 5.5 mm tap and the sixth instrument 222 may be a 6.5 mm tap. Instruments, generally described above as instrument 54 may also include other surgical instruments such as scalpels or scissor instruments 224. Additionally, the instrument 54 may be individually or separately trackable from the handle 210 such as a trackable probe or pointer 226.

The kit 200 may also include various implants or multiple implants which may also be an instrument 54 as discussed herein. It is understood by one skilled in the art, however, that an implant may not be included with various surgical instruments such as a driver handle. Implants may include a first implant 240 that may be a first screw, a second implant 244 may be a second screw, and a third implant 246 may be a third screw. Each of the implants 240, 244, 246 may differ from one another in size, diameter, length, or the like. Other appropriate implants may also include disc replacement implants such as a disc replacement implant 240.

Again, it is understood that the instrument 54 may generally be understood to be any one of a number of instruments that are used during a procedure, as discussed further herein. Moreover, the instruments, including those discussed above in kit 200 may be provided in the single tray 202, a plurality of trays, or no tray and only separately provided. Moreover, instruments used during a procedure may be provided separately from an implant such that surgical preparation instruments may be delivered and prepared separately from the implant to be implanted during a procedure. Regardless, each of the instruments, according to various embodiments, may be identified with the reader system 76 based on a transmission or forwarding of read information from one or more of the readers 40, as discussed further herein.

Regardless of the number, type, packaging, or the like of the instrument 54 provided to the operating theater 20, each is a unique and individual item. Each unique item may, therefore, be specifically and uniquely identified, if selected. Even if more than one type of instrument is provided, each individual instrument may include a unique identity and may be automatically identified as such by the reader system 76.

According to various embodiments, as discussed further herein, the readers 40 may be used to read and transfer or forward identify information to the reader system 76 to identify, uniquely, each of the many instruments provided to the operating theater 20. As discussed herein, the read information may include specific information about the instrument 54 including size, model number, geometry, etc. Alternatively, or in addition thereto, the identity information may include only an identifying number that is compared to a look-up table to determine a unique identity and information about the instrument 54. Further, in various embodiments, the read information may include only an image of all or only a portion of the instrument 54.

If the kit 200 is provided to the operating theater 20, the reader 40 may obtain selected information and transmit the identity information with the communication systems to the reader system 76 for identification of each of the instruments provided in the kit 200 and/or including kit 200. Thus, each instrument 54 moved into the room 20 may have a specific and unique identification information that allows a specific instrument to be identified for various purposes, as discussed herein.

In various embodiments, each of the readers 40 may be visual light cameras (including one or more) which include sensors, such as charge-coupled devices (CCD) and/or complementary metal-oxide-semiconductor (CMOS) sensors. The optical sensors may also, or alternatively, sense invisible light. Further, an image and/or series of images (e.g. video) may be analyzed to uniquely identify the instrument 54, including all of the instruments in the kit 200 or members moved from the kit 200 to selected locations. Other appropriate readers may include microphones to sense or hear sound signals (e.g. audible, ultrasonic, infrasonic) or radio frequency antennas that may transmit or receive radio frequencies, such as in a radio frequency identification (RFID) system. In various embodiments, for example, the reader 40 may be a RFID antenna able to read an indicia that may be an identification portion or member 260 connected or included with each of the members of the kit 200. The ID portion 260, therefore, may be a RFID tag that allows each identifiable instrument to be uniquely identifiable. For example, a first tag 260a may be connected to and/or incorporated into the tray 202. In a similar manner, RFID tag may be incorporated into each of the unique and separate instruments as illustrated in FIG. 2 and or with the tray 202.

When the reader 40 is a RFID antenna, as is generally understood in the art, the reader 40 may transmit a signal that causes an antenna in the ID portion 260 to resonate. Identification information may then be transmitted to the reader 40. The identification information may be transmitted to the reader system 76 for various purposes, as discussed herein. Various RFID tags include those sold by Xerafy company having a place of business in Dallas, Tex. such as the Xerafy RFID tag XS series and/or the DOT XS RFID tag. Further, the reader 40 may include various RFID antenna systems including small or large volume antenna systems. For example, if a small volume antenna or reader is incorporated as the small area readers 40a-40f, they may include the antennas Impinj Speedyway Revolution R420 RFID reader sold by atlasRFIDstore, as discussed above. Various other large area antenna, such as those able to cause a signal to be sent in a selected volume, such as about 5 cubic meters, may include an antenna such as the Impinj Speedway)(Array UHF RFID reader sold by atlasRFIDstore, as discussed above.

In various embodiments, the readers 40 may include visible light cameras including sensors, such as those discussed above. The visible light sensing camera may be provided to obtain a view of the entire operating room 20, such as with the large volume leader 40g or may be used to view a smaller volume, such as substantially only at or near the patient in the operating volume 30, including the smaller volume reader 40d. It is understood that appropriate cameras may also be used as readers 40a, 40b, 40c or other appropriate locations in the operating theater 20. As discussed herein, the readers 40 may include a camera that provide one or more images with visible light for analysis by the reader system 76 to uniquely identify instruments at various locations, such as in preparation for use during the surgery at each of the areas 22, 24, and 26 and/or at the operating volume 50. The visible light images may be the only information provided, according to various embodiments, for determining the unique identification of the instrument. Thus, the instrument 54 may include a visual signature that is used to determine the identity of the instrument 54, as discussed herein.

Figure 3A:
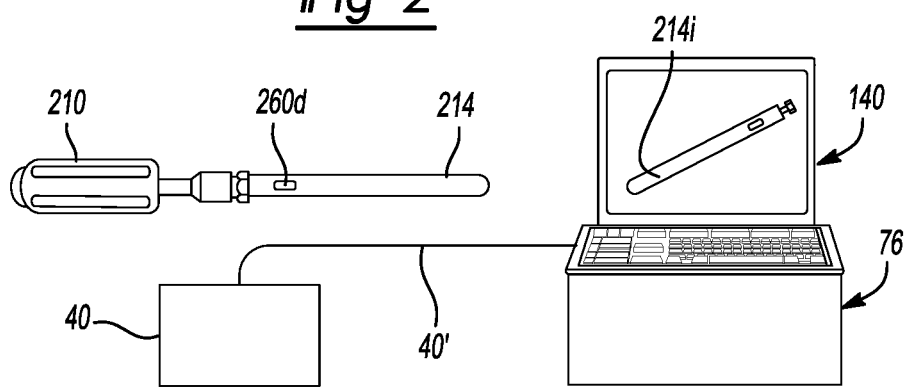
FIG. 3A is an environmental view of an instrument and a reader system for automatic identification of the instrument, according to various embodiments.
Figure 3B:
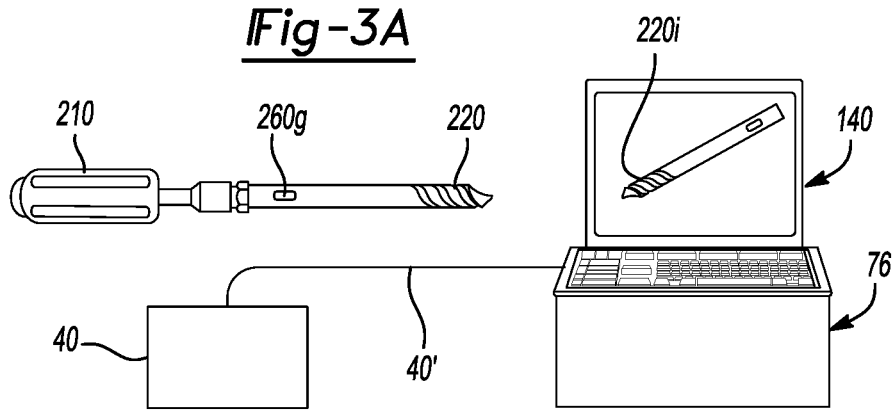
FIG. 3B is an environmental view of an instrument and a reader system for automatic identification of the instrument, according to various embodiments.

The readers 40 allow for the unique and automatic identification of each instrument placed at selected locations or within the room 20. Thus, the specific item that is within the operating field or volume 30 may be identified by one or more of the readers 40. With additional reference to FIGS. 3A and 3B, the reader 40 may read or acquire information regarding the specific instrument for display on the display device 140. It is understood that the display device 140 may be directly connected to reader system 76, as illustrated in FIGS. 3A and 3B, or may be otherwise in communication with the reader system 76. For example, according to various embodiments, the reader system 76 may be in communication with the navigation processor 66. Therefore information from the navigation memory 64 may also be processed by the reader processer 78 and information from the reader system 76 may be transmitted to the navigation processor 66 for display on the display device 140 of the navigation work station 74.

Nevertheless, the reader 40, according to any of the readers discussed above, may read the specific instrument for identification of the specific instrument and transmit the identification to the navigation system 50, such as to the navigation processor 66. In various embodiments, the specifically identified instrument can be illustrated as a related icon, including a specific icon, on the display device 140. Moreover, specific information regarding the specifically identified instrument may be used during navigation of the instrument during a procedure, as is generally understood in the art. For example, a particular instrument may have a length, diameter or width, angular position relative to a tracking device, or other feature or dimension different from a another individual instrument. Therefore, the specific and accurate identification of the particular individual instrument being used at any specific time during a procedure may be useful for a procedure, such as to ensure safety of the subject 34. Moreover, misidentification or an instrument that is not appropriate for use with the navigation system 50 during the procedure, may not be as safe or as desirable as one appropriate and selected for the navigation system 50.

With reference to FIG. 3A a selected individual instrument includes the second instrument 214 attached to the handle 210. The reader 40 may read the instrument 214 and transmit the information to the reader system 76. The reader system 76 may use the transmitted information to determine a specific and unique instrument identification that relates to the instrument 214. In various embodiments, thereafter, an icon 214*i* may be automatically displayed on the display device 140. The icon 214*i* may be a visual representation of the second instrument 214, or may be a representation of a member and a second indication (such as a label) may identify the specific instrument 214. For example, the icon 214*i* may include a display that is substantially identical in appearance to the physical instrument 214 attached to the handle 210. It may further include the specific information regarding length, diameter, and like of the specific instrument 214.

With reference to FIG. 3B, the specific instrument including the first tap 220 is connected to the handle 210. The reader 40 is operable to read the instrument 220 and transmit the information from the reader 40 to the reader system 76. The reader system 76 may use the transmitted information to determine a specific and unique instrument identification that relates to the instrument 220. In various embodiments, thereafter, an icon 220*i* is automatically displayed on the display device 140 regarding the specific instrument 220 attached to the handle 210. Again, the icon 220*i* may include a graphic representation that looks substantially identical to the physical instrument 220 and/or may be a representation of that instrument with additional specific identifying information of the specific instrument 220.

It is further understood by one skilled in the art that an icon representing the specific instrument need not be displayed on the display device 140. In various embodiments, a written or other identification of the specific instrument presented for use may be made. Moreover, as illustrated in FIG. 1, the icon 2214*i* or 220*i* may be used as the icon 160 illustrated relative to the image 146 on the display device 140. Therefore, it is understood that the icon 160 may be any the appropriate icon that is based on the specific instrument read by the reader 40.

The reader 40 may be any appropriate reader, including those as discussed herein. For example, the reader 40 may include a laser scanner that is configured to scan a bar code or other indicia provided on the specific instruments. The indicia may include the indicia 260. In various embodiments the reader 40 may include a scan volume that is configured to scan the indicia 260 to provide read information. The read information may then be transferred to the reader system 76 for further use, as discussed further herein. The reader 40 may also include a RFID antenna that actively receives a signal from the indicia 260 that may be an active transmission RFID tag and/or induces a transmission from the RFID tag as the indicia 260. In various embodiments, therefore, the indicia 260 may be an RFID tag and selected information may be stored thereon that is retrieved by the reader 40 and transferred to the reader system 76. In various embodiments the information stored and received by the reader 40 may include an identification alphanumeric code (e.g. an etched or printed number or word) that is transmitted to the reader system 76. Further, specific identification information, such as specific dimensions, particular identification information, including type of instrument, manufacturer of instrument, or a security code, may be also safely transmitted to the reader 40, such as from the RFID tag.

In various embodiments, the reader 40 may also and/or alternatively include a microphone that receives a sound signal. The sound signal may be an audible, an infrasonic, or an ultrasonic sound signal. The sound signal may be read by the reader 40 and transmitted into the reader system 76. Further, the reader 40 may include a visible light optical camera that is able to view a scene within the room 20, or a selected portion thereof including the areas 22, 24, 26, 30, and 39. The scene may include the instrument 54 alone and/or the indicia 260. For example, the reader 40 may view only the instrument 214 and not the indicia 260. The view of the instrument 214 may be transmitted to the reader system 76 to make a determination of the unique identity of the instrument 214. As discussed herein, various processes may be used for making the determination, such as with a trained neural network including a convolution neural network (CNN). The indicia 260 may also be viewed in the scene by the reader 40 and a determination may be made based on the individual indicia 260 the unique identity of the instrument 214. The indicia 260 may include, therefore, a visible signature that may be incorporated in the CNN for identifying the instrument 54.

With reference to FIG. 4, a use/flowchart 300 is illustrated regarding use of the reader 40 with the reader system 76 in combination with selected outlets for various purposes, including use by the navigation system 50. The reader 40, according to various embodiments as discussed above, may be used to read information, including such as from the indicia 260 and/or directly on the instrument 54, to allow for a determination of the specific instrument, including the instrument 214 or the instrument 220. FIG. 4 in flowchart 300 illustrates an exemplary process, according to various embodiments, for an automatic unique instrument identification and use of the unique instrument identification.

The identification and use process 300 may begin in start block 302. An instrument may be placed in a reader volume or area in block 310. As discussed above, the instrument 54 may be positioned at specific locations, such as at the non-sterile table in area 22 or one or more of the sterile tables or areas 24, 26 or at the operation volume 30. It is further understood that the instrument 54 may be positioned at other locations, such as in the after use location 39, an alternative operating location (e.g., harvest location), or other appropriate locations. As discussed above or herein, therefore, the reader 40 may be used for identifying a general location of the instrument (e.g. at one of the selected locations) and identify whether or not it is ready for use, used, or moved from one or more pre-defined locations. Alternatively, a large area reader, such as the reader 40*g*, may be able to read several individual locations and identify that an instrument is within, such as within a selected error, a particular region. For example, the reader 40*g* may be able to identify that an instrument is within at least 30 cm of a selected area. The large area reader 40*g* need, therefore, not be placed adjacent to or near a specific area, but may be able to read a large area and provide information to the reader system 76 to identify instruments in specific areas and the identity of the specific instruments. In various embodiments, one or more of the large area readers 40*g* may be able to determine and or triangulate (e.g. with a processing system for calculating a location) a location of the instrument within an area, such as in the tray 202, near a preparation area, and/or a surgical area.

When the instrument is placed in a selected reader volume or area in block 310, the instrument may be read in block 314. As discussed above, the instrument may be read in block 314 according to a plurality of manners. In various embodiments, the indicia 260 may include a RFID tag. The RFID tag may include read or write regions that may be accessed by the reader 40. For example, the RFID tag may be read to provide a specific identification number to the reader. Further, the instrument may be read by receiving specific identification information, such as a model number, size, or the like to provide specific information regarding the instrument to the reader system 76. Further, the reader 40 may include an optical camera that images the instrument, such as by being sensitive to visible light. The image of the instrument 54 may include an image of all or a part of the instrument 54 and the image may be transferred as a still image, a series of still images, or a motion video. Further, the reader image of the instrument may be compressed for various purposes to transmit the image data.

The reader images acquired may be used to identify the instrument based upon the all or a portion of the reader image, such as with a trained neural network classification scheme, including a convolution neural network (CNN) system, as is generally understood by one skilled in the art. Various appropriate machine learning and/or neural network systems include the Tensorflow™ open source machine learning system and the Caffe deep learning/machine leaning system as developed at Berkeley Artificial Intelligence Research as a part of University of California. A CNN may be trained and implemented as disclosed in A. Krizhevsky, I. Sutskever, G. E. Hinton, ImageNet Classification with Deep Convolutional Neural Networks, Advances in Neural Information Processing Systems 25 (NIPS 2012), incorporated herein by reference.

A CNN may be implemented on a selected processor system which may include a graphical processing unit (GPU) as a hardware element for training and deploying the CNN. It is understood that a central processor unit (CPU) may also be used to train and implement the CNN. Moreover, the GPU or CPU may be include in the reader system 76, the navigator system 74, or other appropriate processor. Convolutional neural networks, as discussed herein, may be used for object recognition tasks. CNN's allow for training accurate models which are able to cope with image variations such as rotation, scale, illumination, background changes, etc. In various embodiments, the CNN may include a learning module is made that is able to learn from data. A learning database, for the learning module, containing many surgical tool images in different poses, labeled by tool name, type, etc. may be acquired using a camera or a video camera. The CNN may also include a recognition module, namely the use of the CNN previously trained on the training database to recognize, in real time, surgical tools in newly captured images in the operating room. The images are generally visible light images. Moreover, the CNN may be implemented to automatically identify the instrument 54 that is imaged by the reader 40.

In the CNN, in various embodiments, may include and/or account for all information regarding an image, such as including all of the pixels and information regarding the pixels (e.g., color and the like) are convolved in a convolutional layer that may be applied to a depth of an image. The convolutional layers are saved or formed as filters or kernels that may be applied to a newly input image. Therefore, the reader memory 78 may include a plurality of learned instruments (e.g., with imaging an instrument that is identified by a manufacturer prior to the use by the user 58).

In one example, a plurality of images of the instrument 214 may be used for the reader system 76 to "learn" the instrument 214. After learning, when an instrument is read in block 314, the reader processor 68, executing instructions recalled from the reader memory 78, including the CNN regarding the identification of an instrument, may determine, automatically, a unique instrument identification, such as of the specific instrument 214. To determine the instrument identity, a probability of the currently imaged instrument being one of the instruments that trained the CNN may be determined, according to the CNN system. The instrument identity, such as a specific identify of the unique instrument, may be output of the probability is above a selected threshold, such as about 50%, about 60%, or an appropriate or selected probability.

Once the instrument is read in block 314, the transmission of the read information to the reader system 76 may be made in block 320. The transmission of information may include transmission of an ID code from the RFID tag, a barcode number or alphanumeric sequence, or the image of the instrument. The transmitted information from block 320 may be used to identify the specific instrument in block 322, such as by the reader system 76. In various embodiments, the reader memory 78 may include a database, such as a look-up table, that includes information or a correlation or relationship between identities or specific and unique instruments that relate to possible inputs. The database may have identities of one or more specific instrument.

For example, the look-up table may correlate a specific identification number, such as one included on the RFID tag as the indicia 260, to uniquely identify or provide the identity of the specific instrument. In various embodiments, identifying the specific instrument in block 322 may also include the execution of the CNN to identify the specific instrument based upon the transmitted image of the instrument from block 320 read in block 314. The automatic identification may be based on instructions that are executed by a selected processor system, such as those discussed herein, that receive the input and access the database to determine proper outputs for identification, if possible.

It is understood by one skilled in the art, however, that the reading of the instrument 54 in block 314 may be any appropriate reading of information. Identification of the specific instrument in block 322 may be based upon various information, such as accessing a look-up table to compare the look-up table to the read information, using the specific read information (e.g., transmitted specific instrument identification information from a RFID tag, image of the instrument, image of the indicia 260, etc.), or other appropriate information. In various embodiments, however, the identification is automatic by executing the selected instructions, which may also be accessed from a memory, to identify the instrument based on the received or read information. The identification of a specific instrument may then be output, as discussed herein.

Once the instrument is identified in block 322, such as with the reader system 76, the specific instrument identification may be transmitted or used in block 330. The use of the identity of the specific instrument may be according to one or more uses, as discussed further herein. Further, the specific identity of the instrument may be transmitted to other systems, such as the navigation system 50. The navigation system 50 may use the specific identity of the instrument 54 for use in navigating a procedure, as discussed above and further herein. Further transmission of the specific identity of the instrument may be compared to various plans, either in the navigated procedure or in other procedures, as also discussed further herein.

The specific identity of the instrument, such as the instrument 214 illustrated in FIG. 3A, can be used for various purposes from block 330. For example, according to various embodiments, an output of an incorrect, wrong and/or non-approved instrument may be made in block 336. The output of the wrong or incorrect instrument may be for various purposes and may take any appropriate form, such as a visual, tactile, or audible warning. The warning output may further include stopping or freezing navigation and/or removing a display of a representation of the instrument from a display. For example, a predetermined plan for a procedure on the subject 34 may be stored in the navigation memory 64 and/or or the reader memory 76, or other appropriate memory. The specific identity of the instrument, especially when moved to the final prep sterile stage or area 26 and/or the procedure area 30, may be compared to a particular planned stage or point of the procedure (e.g., as identified by the user 58, or such as following the use of a previous instrument) and a warning may be provided that the current instrument is not correct.

Further, a warning may regard that the instrument, such as the instrument 214, is not verified (e.g. properly manufactured, sized, etc.) or appropriate for use with the navigation system 50. For example, the instrument that is identified may be identified as not having been sterilized prior to use. Such a warning may be identified or made when the instrument is moved to the initial or non-sterile area 22. In addition, if the reader system 76 is unable to specifically identify the instrument the warning may also be output. Accordingly, it is understood that the identification of the specific instrument may occur at any location and that various outputs may be made at any appropriate time. Further, it may be identified that the instrument is not appropriate for the particular handle, such as the handle 210, already identified by the reader 76 or input by an appropriate user, such as the user 58. Output warnings, therefore, may include various warnings to the user 58, or other appropriate individual, regarding the specifically identified instrument.

The specifically identified instrument may also be compared to a recalled plan to determine the proper instrument in block 340. As discussed above, an output warning may be that an instrument is incorrect for a particular procedure or predetermined surgical plan and/or that the uniquely identified instrument may be, when compared to the plan, improper at a particular time, not a proper type based upon a previously used instrument, etc. For example, one of the fifth or sixth instrument 220, 222 may include a specific diameter and an implant may be an implant screw such as one of the screws 240, 244, or 246. The identification of the specific instrument, including one of the screws 240, 244, 246, may be compared to the previously used tap 220, 222 to confirm the appropriate size of the read implant. Further, the instrument may include an implant, such as the implant 250. The kit 200 may include a plurality of types of implants, such as sizes, geometries, or specific features, and the identification of the specific instrument in block 322 may be compared to a predetermined plan in block 340 that is recalled from an appropriate memory, such as the navigation memory 64, for performing a procedure.

A previously determined plan, including a previously determined surgical plan for stages of a procedure and the type of implant, may be stored in the navigation memory 64. It is understood that other appropriate plans may also be determined, such as a manner of assembling a device, including a robot assembly, and a car frame, or the like or other appropriate predetermined plan.

Once the comparison is made in block 340, an output of the determination may be made in block 344. The output of the determination may include a warning, similar to the warning output in block 336. The output of the determination in block 344, however, may be based specifically on the comparison of the specifically identified instrument in block 322 when compared to the plan that has also been predetermined. The output may be an auditory output, a visual output (e.g., on the display device 140), or other appropriate output.

The use or transmission of the specific instrument identity may also be received into an instrument management system in block 350 such as for instructing and/or augmenting the instrument management system. For example, the instructing and/or augmenting nay be for updating a database for the instrument management system (e.g. inventory, cleaning regimen, etc.) or instructing actions to be taken place regarding selected instruments or sets of instruments. The instrument management system may be used to save or store that a specific instrument has been used for determining that the instrument 54 must be cleaned prior to a further use and/or that it must be disposed of and reordered for possible future cases of a similar procedure. Additionally, the specifically identified instrument in a selected location, such as on one of the sterile areas 24, 26 and/or in the procedure area 30 and/or in a post-procedure area may also assist in identifying instruments and implants for various purposes such as for compensation, reordering (as discussed above), ensuring that selected instruments are removed from a selected area (e.g., sponges from the procedural area) and other purposes.

Further, the received information in block 350 may be used to compare to a specific procedure to ensure that instruments are prepared for future procedures in block 356. For example, the predetermined plan stored in the navigation memory 64 may be based upon a general plan used by the user 58. Over time, it may be determined that all instruments in the kit 200 are not used and that certain instruments may not be necessary and therefore not provided for use. This may provide for efficient provision of instruments and implants for a procedure. In addition, it may be determined that certain instruments are beneficial to be used during a procedure and those may also be included in the kit 200 for future use. The comparison and determinations may then be stored in block 358 such as in a hospital storage and management system and/or in a specific user storage system.

Further, the use of the specific instrument identity may be transmitted to and received in the navigation system 50 in block 370. It is understood, however, that the reader may be integrated into the navigation system in a selected manner. The received specific identity in block 370 may then be used to display a specific instrument icon in block 374. As discussed above, the display device 140 may display the icon 160, such as the specific instrument icon 214i that relates to the specific instrument 214. The navigation system 50, after receiving the specific identified instrument, may also be used to determine a proper specific instrument based on a recalled predetermined plan, such as a procedure or surgical plan in block 380. The compared plan may be a navigation plan and based upon the use of previously navigated instruments.

Again, the navigation system 50 may access the plan, that may be stored in the navigation memory 64, and compare the current specifically identified instrument, or at least one specifically identified instrument in the procedure area 30, relative to a previously used instrument, such as one moved to a selected location relative to the patient 34. Therefore, although the procedure area 30 may include two taps of two specific sizes, the navigation system 50 may navigate and determine a location of only one of the instruments being moved to form a tapped bore in the subject or patient 34. Therefore, the navigation system 50 may compare not only to previously determined surgical plan, but also a previously used instrument moved to a specific location relative to the subject 34 and compared now to a specifically identified instrument. It is understood, however, that a comparison to only the plan or to only the previously used instrument may be made.

The navigation system 50 and/or the reader system 76 may make the determination that the current read instrument is proper and follow the "yes" block 382 to navigate a planned procedure in block 384. Navigated procedures may be any appropriate procedures, as is generally understood in the art. If a determination that the instrument is not proper, then a "no" path 390 may be followed and an inoperative warning may be made in block 392. The inoperative warning may include stopping navigation, providing a visual or auditory indication of an improper instrument, or other appropriate warnings. Nevertheless, the navigation system 50 may receive the specifically identified instrument from the reader system 76.

As noted above, it is understood that the reader system 76 may automatically identify the specific instrument based upon information received from the reader 40. The instrument 54, or plurality of instruments, may be placed in the reader volume and the reader 40 may read information regarding the instrument 54, such as from indicial 260 and/or an image of the instrument 54, and the read information may be transmitted to the reader system 76 for an automatic identification of the specific instrument. The automatic identification may be the processor 68 executing selected instructions to identify the instrument 54. Selected instructions may include comparing the read information to a look-up table stored in a memory to determine the specific identity of the instrument and/or applying the CNN to determine the identity of an instrument in an image. It is understood that the identity of the instrument 54, however, may be further compared to a look-up table that includes specific information regarding the instrument, such as the geometry or the like of the instrument for use in navigation or other procedures. The identification of the instrument may be substantially automatic by the reader system 76 and providing for various other purposes, as discussed above and illustrated in the flowchart 300.

Automatic identification may allow a user to not be required to otherwise identify the instrument or request the identity of an instrument be input to a navigation system 50 for performing a procedure or for other purposes, such as determining the location of an instrument or the use of an instrument. It is understood, however, that the identification of the instrument in block 322 may also allow a user a final determination, but allow for a display of a limited list of possible identities for a final selection by a selected user, such as the user 58. Moreover, the automatic identification of specific instruments in block 322 may be used for transmitting in block 330 for other purposes such as preparing the navigation 50 for a selected procedure. The navigation system 50 may include various modules or interfaces for different selected procedures, such as one interface and possible instrumentation for a deep-brain simulation and a different interface and possible instrumentation set for a spinal implant. Therefore, the automatic identification of specific instruments in block 322, such as ones placed in a non-sterile area 22, may assist in setting up the navigation system 50 for an appropriate procedure. It is understood, however, that any appropriate system may be set up for a selected procedure based upon the receiving of instruments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

What is claimed is:

1. A system to evaluate instrumentation for use while performing a procedure, comprising:
    an identification member associated with an instrument;
    an identification reader configured to receive an identification signal from the identification member;
    a transmission system configured to transmit a reader signal based on the identification signal relating to the instrument; and
    a processor system to execute instructions to:
        determine an instrument specific identity of the instrument based on the read information;
        determine whether an error is present based on the determined instrument specific identity when positioned in a procedure area; and
        output at least one of the determination of whether an error is present and the determined instrument specific identity of the instrument, wherein the output is operable to be reviewed by a user while performing the procedure.

2. The system of claim 1, wherein the reader signal is the identification signal from the identification member.

3. The system of claim 1, wherein the identification reader includes an antenna configured to induce the identification member to transmit the identification signal.

4. The system of claim 1, further comprising:
    a memory system having stored therein a database of at least one instrument specific identity;
    wherein processor system is configured to execute further instructions to:
        access the database with the transmitted reader signal;
        wherein the determination of the instrument specific identity of the instrument is based on the accessing the database.

5. The system of claim 1, wherein the identification member is fixed to the instrument.

6. The system of claim 1, further comprising:
a tray having a tray identification member associated therewith;
wherein the identification reader is further configured to receive an identification signal from the tray identification member.

7. The system of claim 1, wherein the processor system is operable to execute further instructions to:
output a warning to the user based on the output of the instrument specific identity of the instrument.

8. The system of claim 1,
wherein determining whether the error is present includes determining whether the output of the instrument specific identity of the instrument is a proper instrument when compared to a recalled plan; and
outputting the determination of whether the error is present.

9. The system of claim 1, wherein the processor system is operable to execute further instructions to:
transmit information to an instrument management system based on the output of the instrument specific identity of the instrument and update a predetermined plan including identities of instruments.

10. The system of claim 1, further comprising:
a surgical navigation system having a display device;
wherein the surgical navigation system receives the output of the determined instrument specific identity of the instrument and automatically displays a graphical representation of the specific identity as a graphical icon of the instrument with the display device.

11. The system of claim 1, wherein the identification reader includes at least one of a visual light camera, a sound sensor, radio frequency antennas, or combinations thereof.

12. A method to evaluate instrumentation for use while performing a procedure, comprising:
receiving an identification signal from an identification member with an identification reader, wherein the identification member is associated with an instrument in an area;
executing instructions with a processor system for (i) determining an instrument specific identity of the instrument based on the read information and (ii) determining whether the determined instrument specific identity is indicative of an instrument error for performing the procedure; and
outputting from the processor system (i) the instrument specific identity of the instrument and (ii) an indication of the error if the determined instrument specific identity is determined to be an instrument error for receiving by a user or further analysis while performing the procedure.

13. The method of claim 12, further comprising:
inducing the identification member to transmit the identification signal with a signal sent from an antenna of the identification reader.

14. The method of claim 13, further comprising:
accessing a database of at least one instrument specific identity;
wherein executing instructions with the processor system for determining the instrument specific identity of the instrument includes comparing the received identification signal to the accessed database.

15. The method of claim 12, further comprising:
comparing the output from the processor system of the instrument specific identity of the instrument to a predetermined plan; and
outputting a warning as the indication of the error to the user based on the output of the instrument specific identity of the instrument when it is determined that the determined instrument specific identity is not proper when compared to the predetermined plan.

16. The method of claim 12, further comprising:
receiving the output from the processor system of the instrument specific identity of the instrument at a surgical navigation system to automatically display a representation of the specific identity of the instrument with a display device.

17. A method of performing a procedure, comprising:
transmitting information of an instrument; and
executing instructions with a processor system to:
determine an instrument specific identity of the instrument based on the transmitted information by executing instructions with a processor; and
output the instrument specific identity of the instrument;
preparing a surgical navigation system based on the output the instrument specific identity of the instrument including recalling a predetermined plan including a planned instrument specific identity; and
updating the recalled predetermined plan including updating a list of instruments for the predetermined plan.

18. The method of claim 17, wherein preparing the surgical navigation system further comprises:
executing further instructions with the processor system to compare the output instrument specific identity to a predetermined plan including a planned instrument specific identity;
wherein the processor system is operable to recall the predetermined plan and updating the recalled predetermined plan.

19. The method of claim 17, further comprising:
executing further instructions with a processor system to determine the instrument specific identity of the instrument includes:
training a convolutional neural network to determine at least one filter;
saving the trained convolutional neural network in a memory system;
receiving the transmitted information as an image of the instrument;
applying the at least one filter to the received image of the instrument.

20. The method of claim 17, further comprising:
reading information of the instrument including receiving information from a radio-frequency identification device;
wherein transmitting information of the instrument includes transmitting the received information from the radio-frequency identification device.

21. The method of claim 17, further comprising:
storing the updated recalled predetermined plan.

* * * * *

UNITED STATES PATENT AND TRADEMARK OFFICE
CERTIFICATE OF CORRECTION

PATENT NO. : 10,517,680 B2
APPLICATION NO. : 15/963407
DATED : December 31, 2019
INVENTOR(S) : Moctezuma et al.

Page 1 of 2

It is certified that error appears in the above-identified patent and that said Letters Patent is hereby corrected as shown below:

In the Drawings

Sheet 3 of 3, Fig. 4, Reference Numeral 358, Line 2: Delete "Preperation" and insert --Preparation-- therefor In the Specification Column 2, Drawings, Line 21: Delete "it," and insert --kit,-- therefor Column 2, Detailed Description, Line 57: Delete "nonsterile" and insert --non-sterile-- therefor Column 3, Detailed Description, Line 5: Delete "nonsterile" and insert --non-sterile-- therefor Column 3, Detailed Description, Line 12: Delete "nonsterile" and insert --non-sterile-- therefor Column 3, Detailed Description, Line 14: Delete "44c" and insert --40c-- therefor Column 3, Detailed Description, Line 27: Delete "40a, 40b, 40c, 40d, 40e, 40g, 40h" and insert --40a, 40b, 40c, 40d, 40e, 40f, 40g, 40h-- therefor Column 3, Detailed Description, Line 41: Delete "nonsterile" and insert --non-sterile-- therefor Column 4, Detailed Description, Line 38: Delete "38," and insert --34,-- therefor Column 5, Detailed Description, Line 45: Delete "xArrar" and insert --xArray-- therefor Column 5, Detailed Description, Line 49: Delete "50," and insert --54,-- therefor Column 8, Detailed Description, Line 7: Delete "Speedyway" and insert --Speedway-- therefor Signed and Sealed this
Nineteenth Day of May, 2020

Andrei Iancu
*Director of the United States Patent and Trademark Office*

CERTIFICATE OF CORRECTION (continued)
U.S. Pat. No. 10,517,680 B2

Column 8, Detailed Description, Line 11: Delete "Speedway)(Array" and insert --Speedway xArray-- therefor Column 8, Detailed Description, Line 29: Delete "50." and insert --30.-- therefor Column 8, Detailed Description, Line 49: Delete "processer 78" and insert --processor 68-- therefor Column 9, Detailed Description, Line 43: Delete "2214i" and insert --214i-- therefor Column 11, Detailed Description, Lines 27–28: Delete "leaning" and insert --learning-- therefor Column 13, Detailed Description, Line 15: Delete "76," and insert --78,-- therefor Column 13, Detailed Description, Line 38: After "reader", insert --system--

Column 14, Detailed Description, Line 17: Delete "nay" and insert --may-- therefor Column 15, Detailed Description, Line 32: Delete "indicial" and insert --indicia-- therefor